United States Patent
Chei et al.

(10) Patent No.: US 10,557,034 B2
(45) Date of Patent: Feb. 11, 2020

(54) IONIZING-RADIATION-RESISTANT POLYCARBONATE RESIN COMPOSITION, AND MOLDED PRODUCT COMPRISING SAME

(71) Applicant: LOTTE ADVANCED MATERIALS CO., LTD., Yeosu-si (KR)

(72) Inventors: Woo Suk Chei, Uiwang-si (KR); Hyun Hye Jang, Uiwang-si (KR); Jung Jae Lee, Uiwang-si (KR); Jun Ho Chi, Uiwang-si (KR); Jong Chan Hur, Uiwang-si (KR); O Sung Kwon, Uiwang-si (KR)

(73) Assignee: Lotte Advanced Materials Co., Ltd., Yeosu-si (KR)

( * ) Notice: Subject to any disclaimer, the term of this patent is extended or adjusted under 35 U.S.C. 154(b) by 51 days.

(21) Appl. No.: 15/754,753

(22) PCT Filed: Aug. 30, 2016

(86) PCT No.: PCT/KR2016/009630
§ 371 (c)(1),
(2) Date: Feb. 23, 2018

(87) PCT Pub. No.: WO2017/039273
PCT Pub. Date: Mar. 9, 2017

(65) Prior Publication Data
US 2018/0244914 A1    Aug. 30, 2018

(30) Foreign Application Priority Data
Aug. 31, 2015 (KR) .......................... 10-2015-0122366

(51) Int. Cl.
C08L 69/00    (2006.01)
C08K 5/10    (2006.01)

(52) U.S. Cl.
CPC ................ C08L 69/00 (2013.01); C08K 5/10 (2013.01); C08L 2201/02 (2013.01); C08L 2201/08 (2013.01); C08L 2203/02 (2013.01); C08L 2205/02 (2013.01); C08L 2205/03 (2013.01)

(58) Field of Classification Search
CPC .. C08L 69/00; C08L 2201/02; C08L 2201/08; C08L 2203/02; C08L 2205/02; C08L 2205/03; C08K 5/10
USPC ........................................................ 524/109
See application file for complete search history.

(56) References Cited

U.S. PATENT DOCUMENTS

| | | | |
|---|---|---|---|
| 5,807,908 | A | 9/1998 | Hirose et al. |
| 6,166,116 | A | 12/2000 | Sleeckx |
| 9,216,529 | B2 | 12/2015 | Swinnen et al. |
| 2007/0117957 | A1 | 5/2007 | Mullen |
| 2007/0293600 | A1 | 12/2007 | Tamura |
| 2008/0027167 | A1 | 1/2008 | Vollenberg et al. |
| 2012/0289655 | A1 | 11/2012 | Sumita et al. |
| 2013/0012666 | A1* | 1/2013 | Vollenberg ............ C08L 67/025 525/439 |

FOREIGN PATENT DOCUMENTS

| | | |
|---|---|---|
| CN | 101087848 A | 12/2007 |
| CN | 103717674 A | 4/2014 |
| CN | 102712807 B | 9/2014 |
| JP | 2006-199848 A | 8/2006 |
| KR | 10-2014-0053172 A | 5/2014 |
| WO | 2017/039273 A1 | 3/2017 |

OTHER PUBLICATIONS

Office Action in counterpart Korean Application No. 10-2015-0122366 dated Apr. 12, 2018, pp. 1-5.
International Search Report in counterpart International Application No. PCT/KR2016/009630 dated Nov. 10, 2016, pp. 1-4.
Office Action in counterpart Chinese Application No. 201680049696.4 dated May 27, 2019, pp. 1-7.

* cited by examiner

*Primary Examiner* — William K Cheung
(74) *Attorney, Agent, or Firm* — Additon, Higgins & Pendleton, P.A.

(57) ABSTRACT

A polycarbonate resin composition of the present invention comprises: a polycarbonate resin; a polyalkylene glycol; an epoxy ester compound containing an ester group and an epoxy group; and a halogenated polycarbonate oligomer. The polycarbonate resin composition has excellent discoloration resistance, color, hydrolysis resistance, flame retardancy and the like even after being irradiated with ionizing radiation.

14 Claims, No Drawings

IONIZING-RADIATION-RESISTANT POLYCARBONATE RESIN COMPOSITION, AND MOLDED PRODUCT COMPRISING SAME

CROSS-REFERENCE TO RELATED APPLICATIONS

This application claims priority to and the benefit of International Application No. PCT/KR2016/009630, filed Aug. 30, 2016, which published as WO 2017/039273 on Mar. 9, 2017; and Korean Patent Application No. 10-2015-0122366, filed in the Korean Intellectual Property Office on Aug. 31, 2015, the entire disclosure of each of which is incorporated herein by reference.

TECHNICAL FIELD

The present invention generally relates to an ionizing radiation-resistant polycarbonate resin composition and a molded product comprising the same. More particularly, the present invention relates to an ionizing radiation-resistant polycarbonate resin composition, which has good properties in terms of discoloration resistance, color, hydrolysis resistance and flame retardancy even after irradiation with ionizing radiation, and a molded product comprising the same.

BACKGROUND ART

Polycarbonate resins are broadly used in various fields due to good mechanical and thermal properties thereof. Particularly, polycarbonate resins have good properties in terms of transparency, hygienic properties, rigidity, and heat resistance, and are broadly used as materials for medical supplies for medical devices, surgical instruments, and the like. Such medical products are required to be completely sterilized, and examples of such sterilization methods include contact treatment with sterilized gas such as ethylene oxide, heat treatment in an autoclave, ionizing radiation treatment with gamma radiation, electron beams and X-rays, and the like. Among these methods, contact treatment with ethylene oxide is undesirable due to toxicity and instability of ethylene oxide, and environmental problems caused by waste disposal. In addition, heat treatment in the autoclave can cause deterioration of the polycarbonate resin during treatment at high temperature and requires high energy costs and a drying process due to moisture remaining on a treated part. Therefore, sterilization treatment by irradiation with ionizing radiation, which can be performed at low temperature and is relatively economical, is typically used in the art.

However, it is proposed to stabilize the polycarbonate resin by adding various additives thereto since the polycarbonate resin causes yellowing and property deterioration when irradiated with ionizing radiation. For example, it is known in the art that a polycarbonate resin composition containing a poly(oxyalkylene) derivative and/or a sulfur-containing compound can be stabilized against ionizing radiation for sterilization. Specifically, the polycarbonate resin composition containing a poly(oxyalkylene) derivative and/or a sulfur-containing compound includes a resin composition containing a poly(oxyalkylene) derivative and a disulfide, a resin composition containing a poly(oxyalkylene) derivative and sulfoxide or sulfone, a resin composition containing a poly(oxyalkylene) derivative and a sulfonate, and a resin composition containing a poly(oxyalkylene) derivative and a sulfonamide, and the like.

However, such a polycarbonate resin composition is not sufficiently stabilized against yellowing. Moreover, the polycarbonate resin composition containing a sulfur-containing compound can cause molecular weight reduction, having an adverse effect on the physical properties of the polycarbonate resin.

Therefore, there is a need for development of a polycarbonate resin composition which has good properties in terms of discoloration resistance, color (brightness), hydrolysis resistance and flame retardancy after irradiation with ionizing radiation so as to be applicable to ionizing radiation-resistant medical supplies.

The background technique of the present invention is disclosed in U.S. Pat. No. 6,166,116.

DISCLOSURE

Technical Problem

It is one object of the present invention to provide a polycarbonate resin composition, which has good properties in terms of discoloration resistance, color, hydrolysis resistance and flame retardancy even after irradiation with ionizing radiation, and a molded product comprising the same.

The above and other objects of the present invention can be achieved by the present invention described below.

Technical Solution

One aspect of the present invention relates to a polycarbonate resin composition. The polycarbonate resin composition may include a polycarbonate resin; a polyalkylene glycol; an epoxy ester compound containing an ester group and an epoxy group; and a halogenated polycarbonate oligomer.

In some embodiments, relative to about 100 parts by weight of the polycarbonate resin, the polyalkylene glycol may be present in an amount of about 0.001 to about 5 parts by weight, the epoxy ester compound containing an ester group and an epoxy group is present in an amount of about 0.001 to about 3 parts by weight, and the halogenated polycarbonate oligomer is present in an amount of about 0.01 to about 5 parts by weight.

In some embodiments, the epoxy ester compound containing an ester group and an epoxy group may be a compound represented by Formula 1.

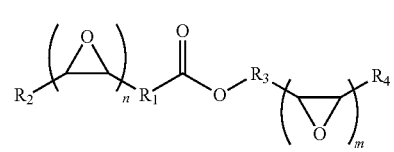

[Formula 1]

In Formula 1, $R_1$ and $R_3$ are each independently a $C_1$ to $C_{10}$ hydrocarbon group; $R_2$ and $R_4$ are each independently a hydrogen atom or $C_1$ to $C_{10}$ hydrocarbon group; m and n are 0 or 1; and m+n is 1 or 2. Here, $R_1$ and $R_2$ and $R_3$ and $R_4$ may be connected to form a ring.

In some embodiments, the halogenated polycarbonate oligomer may include a repeat unit represented by Formula 2:

[Formula 2]

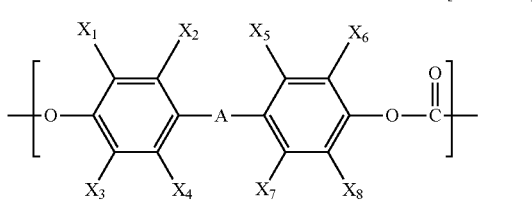

In Formula 2, A is a single bond, a $C_1$ to $C_{20}$ hydrocarbon group, —CO—, —S— or —SO$_2$—; and $X_1$, $X_2$, $X_3$, $X_4$, $X_5$, $X_6$, $X_7$ and $X_8$ are each independently a halogen atom, a hydrogen atom, or a $C_1$ to $C_{10}$ hydrocarbon group, at least one of $X_1$, $X_2$, $X_3$, $X_4$, $X_5$, $X_6$, $X_7$ and $X_8$ being a halogen atom.

In some embodiments, the halogenated polycarbonate oligomer may have a weight average molecular weight of about 600 g/mol to about 10,000 g/mol.

In some embodiments, the halogenated polycarbonate oligomer may contain about 20% by weight (wt %) to about 60 wt % of a halogen based on 100 wt % of the halogenated polycarbonate oligomer.

In some embodiments, the content of the polyalkylene glycol may be about 2 to about 20 times the content of the epoxy ester compound containing an ester group and an epoxy group.

In some embodiments, the polyalkylene glycol and the epoxy ester compound may be present in a total amount of about 0.002 to about 5 parts by weight relative to about 100 parts by weight of the polycarbonate resin.

In some embodiments, the content of the halogenated polycarbonate oligomer may be about 2 to about 15 times the content of the epoxy ester compound containing an ester group and an epoxy group.

In some embodiments, the polycarbonate resin composition may have a yellow index difference (ΔYI) of about 5 or less, as measured on an about 3.2 mm thick specimen and calculated according to Equation 1:

$$\Delta YI = YI_1 - YI_0 \qquad \text{[Equation 1]}$$

In Equation 1, $YI_0$ is a yellow index (YI) of the specimen, as measured in accordance with ASTM D1925 before irradiation with γ-rays, and $YI_1$ is a yellow index (YI) of the specimen, as measured in accordance with ASTM D1925 after irradiation with γ-rays at about 25 kGy and leaving the specimen for about 7 days.

In some embodiments, the polycarbonate resin composition may have a brightness (L*) of about 80 or more, as measured on an about 3.2 mm thick specimen in accordance with ASTM D2244 after irradiation with γ-rays at about 25 kGy and leaving the specimen for about 7 days.

In some embodiments, the polycarbonate resin composition may have a weight average molecular weight difference of about 2,000 g/mol or less, as measured on an about 3.2 mm thick specimen after steam treatment at about 120° C. and about 2 bar for about 16 hours.

In some embodiments, the polycarbonate resin composition may have a flame retardancy of V-1 or more, as measured on an about 2.5 mm thick specimen in accordance with the UL-94 vertical test method.

Another aspect of the present invention relates to a molded product formed of the polycarbonate resin composition.

In some embodiments, the molded product may be an ionizing radiation-resistant medical appliance.

Advantageous Effects

The present invention provides a polycarbonate resin composition which has good properties in terms of discoloration resistance, color, hydrolysis resistance and flame retardancy even after irradiation with ionizing radiation, and a molded product comprising the same. The molded product can be advantageously used as an ionizing radiation-resistant medical appliance.

BEST MODE

Hereinafter, embodiments of the present invention will be described in detail.

A polycarbonate resin composition according to the present invention has ionizing radiation-resistance, and includes: (A) a polycarbonate resin; (B) a polyalkylene glycol; (C) an epoxy ester compound containing an ester group and an epoxy group; and (D) a halogenated polycarbonate oligomer.

(A) Polycarbonate Resin

The polycarbonate resin may include any suitable polycarbonate resin such as an aromatic polycarbonate resin used in a typical polycarbonate resin composition. The polycarbonate resin may be prepared by a typical method, for example, by reacting a dihydric phenol compound with phosgene or through transesterification of a dihydric phenol compound and a carbonate precursor such as diphenyl carbonate.

In preparation of the polycarbonate resin, the dihydric phenol compound may be a bisphenol compound, for example, 2,2-bis(4-hydroxyphenyl)propane (hereinafter, "bisphenol A"). Here, the bisphenol A may be partially or completely replaced by other dihydric phenol compounds. Examples of the other dihydric phenol compounds may include hydroquinone, 4,4'-biphenol, bis(4-hydroxyphenyl)methane, 1,1-bis(4-hydroxyphenyl)cyclohexane, 2,2-bis(3-methyl-4-hydroxyphenyl)propane, 2,2-bis(3,5-dimethyl-4-hydroxyphenyl)propane, bis(4-hydroxyphenyl)sulfide, bis(4-hydroxyphenyl)sulfone, bis(4-hydroxyphenyl)sulfoxide, bis(4-hydroxyphenyl)ketone, bis(4-hydroxyphenyl)ether, and the like. However, the dihydric phenol compound that can be used for preparation of the polycarbonate resin is not limited thereto, and the polycarbonate resin may be prepared using any dihydric phenol compound.

In addition, the polycarbonate resin may be a homopolymer obtained using one dihydric phenol compound, a copolymer obtained using at least two dihydric phenol compounds, or a mixture thereof.

Furthermore, the polycarbonate resin may be a linear polycarbonate resin, a branched polycarbonate resin, or a polyester carbonate copolymer resin. The polycarbonate resin included in the polycarbonate resin composition according to the present invention may include such linear polycarbonate resins, branched polycarbonate resins, and polyester carbonate copolymer resins, without being limited thereto.

For example, the linear polycarbonate resin may be a bisphenol A polycarbonate resin, and the branched polycarbonate resin may be prepared by, for example, reacting a polyfunctional aromatic compound such as trimellitic anhydride or trimellitic acid with a dihydric phenol compound and a carbonate precursor. The polyester carbonate copolymer resin may be prepared by, for example, reacting a bifunctional carboxylic acid with a dihydric phenol and a carbonate precursor. In addition, the polycarbonate resin may include typical linear polycarbonate resins, branched polycarbonate resins, and polyester carbonate copolymer resins without limitation.

In some embodiments, the polycarbonate resin may include a terminal modified polycarbonate resin having a tert-butylphenoxy group at a terminal thereof. The terminal modified polycarbonate resin may be prepared by a typical method for preparing the polycarbonate resin except that tert-butylphenol is added in the preparation of the polycarbonate resin. When the terminal modified polycarbonate resin is included in the composition, the tert-butylphenoxy group may be present in an amount of about 0.1 mol % to about 80 mol %, for example, about 20 mol % to about 60 mol %, in the polycarbonate resin. Within this range, the polycarbonate resin composition can exhibit further enhanced properties in terms of ionizing radiation resistance, impact resistance, and the like.

In some embodiments, the polycarbonate resin may have a weight average molecular weight (Mw) of about 10,000 g/mol to about 200,000 g/mol, for example, about 15,000 g/mol to about 80,000 g/mol, as measured by gel permeation chromatography (GPC), without being limited thereto.

In addition, the polycarbonate resin may have a melt flow index (MI) of about 3 g/10 min to about 35 g/10 min, as measured in accordance with ISO 1133 (at about 300° C. under a load of about 1.2 kg), without being limited thereto.

(B) Polyalkylene Glycol

The polyalkylene glycol may include polyalkylene glycol, ethers of polyalkylene glycol, and/or esters of polyalkylene glycol. The polyalkylene glycol compound may include any polyols used in a typical ionizing radiation resistant composition. Examples of the polyols may include polyethylene glycol, polyethylene glycol methyl ether, polyethylene glycol dimethyl ether, polyethylene glycol dodecyl ether, polyethylene glycol benzyl ether, polyethylene glycol dibenzyl ether, polyethylene glycol-4-nonylphenylether, polypropylene glycol, polypropylene glycol methyl ether, polypropylene glycol dimethyl ether, polypropylene glycol dodecyl ether, polypropylene glycol benzyl ether, polypropylene glycol dibenzyl ether, polypropylene glycol-4-nonylphenylether, polytetramethylene glycol, polyethylene glycol diacetate, polyethylene glycol acetate propionate, polyethylene glycol dibutyrate, polyethylene glycol distearate, polyethylene glycol dibenzoate, polyethylene glycol di-2,6-dimethyl benzoate, polyethylene glycol di-p-tert-butyl benzoate, polyethylene glycol dicaprylate, polypropylene glycol diacetate, polypropylene glycol acetate propionate, polypropylene glycol dibutyrate, polypropylene glycol distearate, polypropylene glycol dibenzoate, polypropylene glycol di-2,6-dimethyl benzoate, polypropylene glycol di-p-tert-butyl benzoate, and polypropylene glycol dicaprylate, without being limited thereto. These may be used alone or as a mixture thereof.

In some embodiments, the polyalkylene glycol may have a number average molecular weight (Mn) of about 1,000 g/mol to about 5,000 g/mol, for example, about 1,500 g/mol to about 3,000 g/mol, as measured by gel permeation chromatography (GPC).

In some embodiments, the polyalkylene glycol may be present in an amount of about 0.001 to about 5 parts by weight, for example, about 0.01 to about 4 parts by weight, relative to about 100 parts by weight of the polycarbonate resin. Within this range, the polycarbonate resin composition can exhibit good properties in terms of discoloration resistance after irradiation with ionizing radiation.

(C) Epoxy Ester Compound

In the polycarbonate resin composition according to the present invention, the epoxy ester compound containing an ester group and an epoxy group serves to enhance ionizing radiation resistance without deterioration in hydrolysis resistance, and may include a compound represented by, for example, Formula 1.

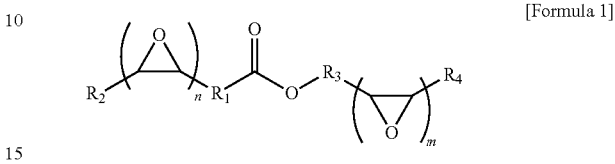

[Formula 1]

In Formula 1, $R_1$ and $R_3$ are each independently a $C_1$ to $C_{10}$ hydrocarbon group; $R_2$ and $R_4$ are each independently a hydrogen atom or $C_1$ to $C_{10}$ hydrocarbon group; m and n are 0 or 1; and m+n is 1 or 2. Here, $R_1$ and $R_2$ and $R_3$ and $R_4$ may be connected to form a ring.

Examples of the epoxy ester compound containing an ester group and an epoxy group may include compounds represented by Formulae 1a to 1c, without being limited thereto.

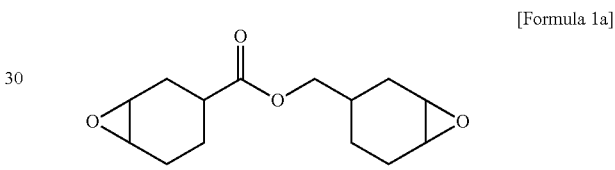

[Formula 1a]

[Formula 1b]

[Formula 1c]

In some embodiments, the epoxy ester compound containing an ester group and an epoxy group may be present in an amount of about 0.001 to about 3 parts by weight, for example, about 0.01 to about 2 parts by weight, relative to about 100 parts by weight of the polycarbonate resin. Within this range, the polycarbonate resin composition can exhibit good properties in terms of discoloration resistance without deterioration in hydrolysis resistance and thermal stability even after irradiation with ionizing radiation.

In addition, the content of the polyalkylene glycol may be about 2 to about 20 times the content of the epoxy ester compound containing an ester group and an epoxy group, and the polyalkylene glycol and the epoxy ester compound may be present in a total amount of about 0.002 to about 5 parts by weight, for example, about 0.02 to about 3 parts by weight, relative to about 100 parts by weight of the polycarbonate resin. Within this range, the polycarbonate resin composition can exhibit good properties in terms of discoloration resistance without deterioration in hydrolysis resistance and thermal stability after irradiation with ionizing radiation.

(D) Halogenated Polycarbonate Oligomer

In the polycarbonate resin composition according to the present invention, the halogenated polycarbonate oligomer serves to enhance ionizing radiation-resistance and flame retardancy, and may be prepared using a halogen atom-containing dihydric phenol compound, phosgene, a carbonate precursor such as diphenyl carbonate, and the like.

In some embodiments, the halogenated polycarbonate oligomer may include a repeat unit represented by Formula 2.

[Formula 2]

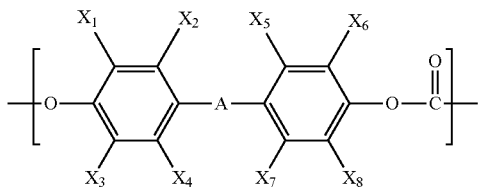

In Formula 2, A is a single bond, a $C_1$ to $C_{20}$ hydrocarbon group, for example, a $C_1$ to $C_{20}$ alkylene group, a $C_2$ to $C_5$ alkylidene group, a $C_5$ to $C_6$ cycloalkylene group, a $C_5$ to $C_6$ cycloalkylidene group, —CO—, —S— or —SO$_2$—; and $X_1$, $X_2$, $X_3$, $X_4$, $X_5$, $X_6$, $X_7$ and $X_8$ are each independently a halogen atom such as Cl or Br, a hydrogen atom, or a $C_1$ to $C_{10}$ hydrocarbon group, at least one of $X_1$, $X_2$, $X_3$, $X_4$, $X_5$, $X_6$, $X_7$ and $X_8$ being a halogen atom.

In some embodiments, the halogenated polycarbonate oligomer may be prepared using the halogen atom-containing dihydric phenol compound and the carbonate precursor through a typical polymerization method known in the art. Examples of the halogen atom-containing dihydric phenol compound include bis(4-hydroxy-3,5-dibromophenyl)methane, 2,2-bis(4-hydroxy-3,5-dibromophenyl)propane, 4,4'-dihydroxy-3,3',5,5'-tetrabromodiphenylsulfide, 2,2-bis(4-hydroxy-3,5-dichlorophenyl)propane, 2,2-bis(4-hydroxy-3-bromophenyl)propane, bis(4-hydroxy-3-chlorophenyl) methane, bis(4-hydroxy-3-bromo phenyl)methane, and combinations thereof.

In some embodiments, the halogenated polycarbonate oligomer may have a weight average molecular weight (Mw) of about 600 g/mol to about 10,000 g/mol, for example, about 1,000 g/mol to about 6,000 g/mol, as measured by gel permeation chromatography (GPC), without being limited thereto. Within this range, the polycarbonate resin composition can have improved discoloration resistance and flame retardancy even after irradiation with ionizing radiation.

In some embodiments, the halogenated polycarbonate oligomer may contain about 20 to about 60 wt % of a halogen, for example, about 30 to about 60 wt %, based on 100 wt % of the halogenated polycarbonate oligomer, as measured by ion chromatography. Within this range, the polycarbonate resin composition can have improved discoloration resistance and flame retardancy even after irradiation with ionizing radiation.

In some embodiments, the halogenated polycarbonate oligomer may be present in an amount of about 0.01 to about 5 parts by weight, for example, about 0.05 to about 2 parts by weight, relative to about 100 parts by weight of the polycarbonate resin. Within this range, it is possible to obtain a polycarbonate resin composition having improved discoloration resistance and flame retardancy even after irradiation with ionizing radiation.

The content of the halogenated polycarbonate oligomer may be about 2 to about 15 times the content of the epoxy ester compound containing an ester group and an epoxy group. Within this range, the polycarbonate resin composition can exhibit good properties in terms of discoloration resistance without deterioration in hydrolysis resistance and thermal stability even after irradiation with ionizing radiation.

The polycarbonate resin composition according to one embodiment may further include an ally ether compound.

The ally ether compound may include trimethylolpropane diallyl ether, pentaerythritol diallyl ether, glycerin diallyl ether, and mixtures thereof, without being limited thereto.

In some embodiments, the ally ether compound may be present in an amount of about 0.001 to about 3 parts by weight, for example, about 0.01 to about 2 parts by weight, relative to about 100 parts by weight of the polycarbonate resin. Within this range, the polycarbonate resin composition can exhibit further enhanced discoloration resistance even after irradiation with ionizing radiation.

The polycarbonate resin composition according to the present invention may further include another resin without deteriorating advantageous effects of the present invention. For example, polyethylene terephthalate, polybutylene terephthalate, polyester polycarbonate, and the like may be further added to the polycarbonate resin composition, without being limited thereto. When the polycarbonate resin composition further includes these resins, these resins may be present in an amount of about 50 parts by weight or less, for example, about 1 to about 15 parts by weight, relative to about 100 parts by weight of the polycarbonate resin, without being limited thereto.

The polycarbonate resin composition may further include additives which are typically used in a resin composition. Examples of the additives may include fillers, a reinforcing agent, a stabilizer, a coloring agent, an antioxidant, an antistatic agent, a flow improver, a release agent, and a nucleation agent, without being limited thereto. The additives may be used in an amount of about 25 parts by weight or less, for example, about 5 parts by weight or less, relative to about 100 parts by weight of the polycarbonate resin, without being limited thereto.

The polycarbonate resin composition may be prepared by a method for preparing a thermoplastic resin known in the art. For example, the polycarbonate resin composition may be prepared in pellet form by mixing the components of the polycarbonate resin composition as set forth above with other additives, followed by melt extrusion using an extruder, and the like. The prepared pellets may be formed into various products by various molding methods, such as injection molding, extrusion molding, vacuum molding, casting, and the like.

In one embodiment, the polycarbonate resin composition according to the present invention may have a yellow index difference ΔYI of about 5 or less, for example, about −2 to about 2.5, as measured on an about 3.2 mm thick specimen and calculated according to Equation 1.

$$\Delta YI = YI_1 - YI_0 \qquad \text{[Equation 1]}$$

In Equation 1, $YI_0$ is the yellow index (YI) of the specimen, as measured in accordance with ASTM D1925 before irradiation with γ-rays, and $YI_1$ is the yellow index (YI) of the specimen, as measured in accordance with ASTM D1925 after irradiation with γ-rays at about 25 kGy and leaving the specimen for about 7 days.

In some embodiments, the polycarbonate resin composition may have a brightness (L*) of about 80 or more, for example, about 85 to about 95, as measured on an about 3.2 mm thick specimen in accordance with ASTM D2244 after irradiation with γ-rays at about 25 kGy and leaving the specimen for about 7 days.

In some embodiments, the polycarbonate resin composition may have a weight average molecular weight difference of about 2,000 g/mol or less, for example, about 100 g/mol to about 1,900 g/mol, as measured on an about 3.2 mm thick specimen of the polycarbonate resin composition after steam treatment under conditions of about 120° C. and about 2 bar for about 16 hours.

In some embodiments, the polycarbonate resin composition may have a flame retardancy of V-1 or more, for example, V-1 to V-0, as measured on an about 2.5 mm thick specimen in accordance with the UL-94 vertical test method.

A molded product according to the present invention may be formed of the ionizing radiation resistant polycarbonate resin composition by a molding method known in the art. The molded product exhibits excellent properties in terms of ionizing radiation resistance, hydrolysis resistance, flame retardancy, impact resistance, and the like. Thus, the molded product according to the present invention may be advantageously used in ionizing radiation resistant medical appliances including container-type packages for receiving or packing syringes, surgical instruments, intravenous injectors and surgical devices, components of medical devices, such as artificial lungs, artificial kidneys, anesthesia inhalers, vein couplers, hemodialyzers, hemofilters, safety syringes and components thereof, and components of blood centrifuges, surgical instruments, surgical instruments, intravenous injectors, and the like.

MODE FOR INVENTION

Next, the present invention will be described in more detail with reference to some examples. It should be understood that these examples are provided for illustration only and are not to be construed in any way as limiting the present invention.

Descriptions of details apparent to those skilled in the art will be omitted for clarity.

EXAMPLE

A polycarbonate resin, a polyalkylene glycol, an epoxy ester compound and a halogenated polycarbonate oligomer used in the following examples and comparative examples are as follows.

(A) Polycarbonate Resin

A bisphenol A based polycarbonate resin (weight average molecular weight (Mw): 28,000 g/mol, melt-flow index (MI): 8 g/10 min (300° C., load: 1.2 kg)) was used.

(B) Polyalkylene Glycol

Polypropylene glycol (number average molecular weight (Mn): 2,000 g/mol) was used.

(C) Epoxy Ester Compound Containing an Ester Group and an Epoxy Group

A compound represented by Formula 1a was used.

[Formula 1a]

(D) Halogenated Polycarbonate Oligomer

An oligomer (weight average molecular weight (Mw): 5,000 g/mol) comprising a repeat unit represented by Formula 2a was used.

[Formula 2a]

Examples 1 to 2 and Comparative Examples 1 to 3: Preparation of Polycarbonate Resin Composition As listed in the following Table 1, the polycarbonate resin (A), the polyalkylene glycol (B), the epoxy ester compound containing an ester group and an epoxy group (C), and the halogenated polycarbonate oligomer (D) were blended, followed by extrusion molding using a twin-screw extruder (L/D=36, (D=32 mm) at 270° C., thereby preparing a polycarbonate resin composition which was produced into pellets through a pelletizer. The pellet-shaped polycarbonate resin composition was dried in an oven at 100° C. for 2 hours, followed by injection molding in an injection molding machine (DHC 120WD, Dongshin Hydraulics Co.) at a molding temperature of 270° C. and a mold temperature of 70° C. to prepare a specimen. Properties of the prepared specimen were evaluated by the following methods, and results are shown in Table 1.

Property Evaluation (1) Discoloration resistance: In accordance with ASTM D1925, the yellow indices YI of a 3.2 mm thick specimen of each of the polycarbonate resin compositions were measured before irradiation with γ-rays, and 1 day and 7 days after irradiation with γ-rays, followed by calculating a yellow index difference ΔYI according to Equation 1.

$$\Delta YI = YI_1 - YI_0 \quad \text{[Equation 1]}$$

In Equation 1, $YI_0$ is the yellow index (YI) of the 3.2 mm thick specimen, as measured in accordance with ASTM D1925 before irradiation with γ-rays, and $YI_1$ is the yellow index (YI) of the specimen, as measured in accordance with ASTM D1925 after irradiation with γ-rays at about 25 kGy and leaving the specimen for 1 day and 7 days.

(2) Color (brightness) evaluation: Brightness (L*) of a 3.2 mm thick specimen of each of the polycarbonate resin compositions was measured in accordance with ASTM D2244 after irradiating the specimen with γ-rays at 25 kGy and leaving the specimen for 1 day and 7 days.

(3) Hydrolysis resistance evaluation (moist heat evaluation): The weight average molecular weight (Mw) of a 3.2 mm thick specimen of each of the polycarbonate resin compositions was measured by GPC (gel permeation chromatography). Then, the specimen was placed in an autoclave and maintained under steam conditions of 2 bar and 120° C. for 16 hours, followed by measurement of the weight average molecular weight. Then, a weight average molecular weight difference ΔMw between before and after moist heat evaluation was calculated.

(4) Flame retardancy: Flame retardancy was measured on a 2.5 mm thick specimen by the UL-94 vertical test method.

TABLE 1

|  |  | Example 1 | Example 2 | Comparative Example 1 | Comparative Example 2 | Comparative Example 3 |
|---|---|---|---|---|---|---|
| (A) (parts by weight) | | 100 | 100 | 100 | 100 | 100 |
| (B) (parts by weight) | | 0.7 | 0.7 | 0.7 | 0.7 | 0.6 |
| (C) (parts by weight) | | 0.05 | 0.05 | — | — | 0.05 |
| (D) (parts by weight) | | 0.6 | 0.3 | — | 0.6 | — |
| Δ YI before and after irradiation with γ-rays | 1 day | 3.4 | 12 | 39.1 | 5.2 | 22 |
| | 7 days | −0.9 | 2.0 | 20.3 | 1.2 | 3.2 |
| L* after irradiation with γ-rays | 1 day | 84 | 81 | 75 | 80 | 80 |
| | 7 days | 90 | 84 | 80 | 84 | 86 |
| Moist heat evaluation | Δ Mw | 1,500 | 1,800 | 2,000 | 3,000 | 1,000 |
| Flame retardancy | | V-0 | V-1 | V-2 | V-0 | V-2 |

From the results shown in Table 1, it can be seen that the polycarbonate resin compositions (Examples 1 and 2) according to the present invention had a yellow index difference ΔYI (7 days) of 2 or less after irradiation with ionizing radiation, a brightness (L*) of 84 or more after irradiation with ionizing radiation, a weight average molecular weight difference ΔMw of 1,800 g/mol or less after moist heat evaluation, and a flame retardancy of V-1 or more, thereby exhibiting excellent properties in terms of discoloration resistance, color, hydrolysis resistance, and flame retardancy after irradiation with ionizing radiation.

Conversely, the polycarbonate resin composition of Comparative Example 1, which did not include the epoxy ester compound (C) and the halogenated polycarbonate oligomer (D), exhibited deterioration in discoloration resistance, flame retardancy, and hydrolysis resistance (moist heat stability) after irradiation with ionizing radiation; the polycarbonate resin composition of Comparative Example 2, which did not include the epoxy ester compound (C), exhibited deterioration in hydrolysis resistance after irradiation with ionizing radiation; and the polycarbonate resin composition of Comparative Example 3, which did not include the halogenated polycarbonate oligomer (D), exhibited deterioration in discoloration resistance and flame retardancy after irradiation with ionizing radiation.

It should be understood that various modifications, changes, alterations, and equivalent embodiments can be made by those skilled in the art without departing from the spirit and scope of the invention.

The invention claimed is:

1. A polycarbonate resin composition comprising:
about 100 parts by weight of a polycarbonate resin;
about 0.001 to about 5 parts by weight of a polyalkylene glycol;
about 0.001 to about 3 parts by weight of an epoxy ester compound containing an ester group and an epoxy group; and
about 0.01 to about 5 parts by weight of a halogenated polycarbonate oligomer.

2. The polycarbonate resin composition according to claim 1, wherein the epoxy ester compound containing an ester group and an epoxy group is a compound represented by Formula 1:

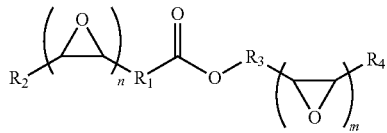

[Formula 1]

where $R_1$ and $R_3$ are each independently a $C_1$ to $C_{10}$ hydrocarbon group; $R_2$ and $R_4$ are each independently a hydrogen atom or $C_1$ to $C_{10}$ hydrocarbon group; m and n are 0 or 1; and m+n is 1 or 2, wherein $R_1$ and $R_2$ and/or $R_3$ and $R_4$ are optionally connected to form a ring.

3. The polycarbonate resin composition according to claim 1, wherein the halogenated polycarbonate oligomer comprises a repeat unit represented by Formula 2:

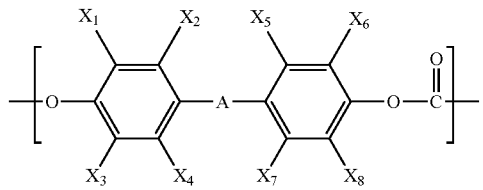

[Formula 2]

where A is a single bond, a $C_1$ to $C_{20}$ hydrocarbon group, —CO—, —S— or —$SO_2$—; and $X_1$, $X_2$, $X_3$, $X_4$, $X_5$, $X_6$, $X_7$ and $X_8$ are each independently a halogen atom, a hydrogen atom, or a $C_1$ to $C_{10}$ hydrocarbon group, with the proviso that at least one of $X_1$, $X_2$, $X_3$, $X_4$, $X_5$, $X_6$, $X_7$ and $X_8$ is a halogen atom.

4. The polycarbonate resin composition according to claim 1, wherein the halogenated polycarbonate oligomer has a weight average molecular weight of about 600 g/mol to about 10,000 g/mol.

5. The polycarbonate resin composition according to claim 1, wherein the halogenated polycarbonate oligomer comprises about 20 wt % to about 60 wt % of a halogen based on 100 wt % of the halogenated polycarbonate oligomer.

6. The polycarbonate resin composition according to claim 1, wherein the content of the polyalkylene glycol is about 2 to about 20 times the content of the epoxy ester compound containing an ester group and an epoxy group.

7. The polycarbonate resin composition according to claim 1, wherein the polyalkylene glycol and the epoxy ester compound are present in a total amount of about 0.002 to about 5 parts by weight relative to about 100 parts by weight of the polycarbonate resin.

8. The polycarbonate resin composition according to claim 1, wherein the content of the halogenated polycarbonate oligomer is about 2 to about 15 times the content of the epoxy ester compound containing an ester group and an epoxy group.

9. The polycarbonate resin composition according to claim 1, wherein the polycarbonate resin composition has a yellow index difference (ΔYI) of about 5 or less, as measured on an about 3.2 mm thick specimen and calculated according to Equation 1:

$$\Delta YI = YI_1 - YI_0$$

where $YI_0$ is a yellow index (YI) of the specimen, as measured in accordance with ASTM D1925 before irradiation with γ-rays, and $YI_1$ is a yellow index (YI) of the specimen, as measured in accordance with ASTM D1925 after irradiation with γ-rays at about 25 kGy and leaving the specimen for about 7 days.

10. The polycarbonate resin composition according to claim 1, wherein the polycarbonate resin composition has a brightness (L*) of about 80 or more, as measured on an about 3.2 mm thick specimen in accordance with ASTM D2244 after irradiation with γ-rays at about 25 kGy and leaving the specimen for about 7 days.

11. The polycarbonate resin composition according to claim 1, wherein the polycarbonate resin composition has a weight average molecular weight difference of about 2,000 g/mol or less, as measured on an about 3.2 mm thick specimen after steam treatment at about 120° C. and about 2 bar for about 16 hours.

12. The polycarbonate resin composition according to claim 1, wherein the polycarbonate resin composition has a flame retardancy of V-1 or more, as measured on an about 2.5 mm thick specimen in accordance with the UL-94 vertical test method.

13. A molded product formed of the polycarbonate resin composition according to claim 1.

14. The molded product according to claim 13, wherein the molded product is an ionizing radiation-resistant medical appliance.

* * * * *